United States Patent [19]
Wakabayashi et al.

[11] 3,994,938
[45] Nov. 30, 1976

[54] PROCESS FOR PRODUCING STEROIDAL COMPOUNDS

[75] Inventors: Ken-ichi Wakabayashi, Machida; Yasuhiro Chigira, Yokohama; Kaoru Fukuda, Sagamihara, all of Japan

[73] Assignee: Mitsubishi Chemical Industries Ltd., Tokyo, Japan

[22] Filed: Aug. 8, 1975

[21] Appl. No.: 602,810

[30] Foreign Application Priority Data

Aug. 22, 1974  Japan.............................. 49-96350

[52] U.S. Cl............................ 260/397.4; 260/397.5
[51] Int. Cl.².......................................... C07J 1/00
[58] Field of Search...................... 260/397.4, 397.5

[56] References Cited
OTHER PUBLICATIONS

Steroid Reactions (Dyerassi) 1963, pp. 382, 383, 399–402.

*Primary Examiner*—Elbert L. Roberts
*Attorney, Agent, or Firm*—Oblon, Fisher, Spivak, McClelland & Maier

[57] ABSTRACT

Steroidal 19-nor-3-hydroxy-1, 3, 5(10)-trienes are produced by a process which comprises admixing a preheated hydrocarbon and a solution of a steroidal 10-methyl-1, 4-diene-3-one dissolved or suspended in a hydrocarbon, and then pyrolyzing said steroidal compound.

15 Claims, 1 Drawing Figure

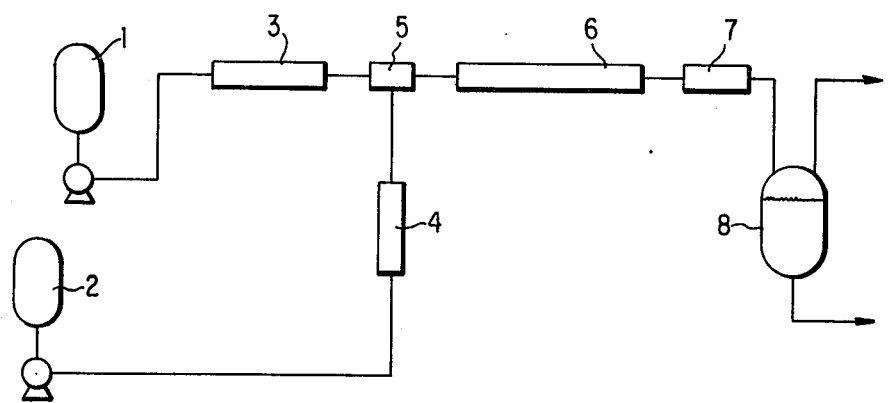

PROCESS FOR PRODUCING STEROIDAL COMPOUNDS

BACKGROUND OF THE INVENTION

1. Field of the Invention:

The present invention relates to an improved process for producing steroidal compounds by converting a steroidal 10-methyl-1, 4-dien-3-one to a steroidal 19-nor-3-hydroxy-1,3,5(10)-triene.

2. Description of the Prior Art:

The steroidal 19-nor-3-hydroxy-1,3,5(10)-trienes produced by the process of the present invention, particularly 3-hydroxyestra-1,3,5(10)-trien-17-one (estrone) are useful as ovarian hormones and as intermediates for preparation of steroidal hormones such as ethisterone. Ethisterone is important as a main component of oral contraceptive pills.

It is known that estrone is produced by the pyrolysis of androst-1,4-dien-3, 17-dione which is one of the steroidal 10-methyl-1, 4-dien-3-ones.

There are also known processes wherein estrone is produced by feeding a solution of androst-1, 4-dien-3, 17-dione dissolved in decalin, tetralin, cyclohexane, a higher aliphatic hydrocarbon or mineral oil into a glass tower reactor having a length to diameter ratio of from 10 to 15, and optionally packed with glass, and thereafter pyrolyzing the solution. (J. Org. Chem., 15 292 (1950); J. Am. Chem. Soc., 72 4531 (1953); U.S. Pat. No. 2,594,349). However, such processes suffer from the significant disadvantage of low selectivity. Yields are only 40 – 60 percent. Another hindrance to the commercial development of such processes for the production of estrone is the difficulty in industrial production of providing sufficient heating surface to heat the reaction mixture to the reaction temperature. The low selectivity of these processes has been shown to arise from the thermal instabilities of androst-1, 4-dien-3, 17-dione and estrone.

Through studying the high temperature stability of these compounds it has been found that unnecessarily prolonged heating at temperatures above 300° C will result in an increase in the amount of unfavorable by-products. On the other hand, the compounds are stable at temperatures below 300° C for long periods of time.

In order to avoid the unfavorable side reactions, it is necessary, therefore, to heat the reaction mixture rapidly to the reaction temperature. This may be accomplished by providing sufficient heating surface, which is, however, almost impossible in the industrial production of estrone. Consequently, a solution to this problem would be most desirable.

SUMMARY OF THE INVENTION

Accordingly, it is an object of this invention to produce steroidal 19-nor-3-hydroxy-1,3,5(10)-trienes economically and in high yields by a process suitable for industrial use.

Briefly, this and other objects of this invention, as will hereinafter be made clear from the ensuing discussion, have been attained by providing a process wherein steroidal 19-nor-3-hydroxy-1,3,5(10)-trienes are produced in high yields by admixing a solution of a steroidal 10-methyl-1, 4-dien-3-one dissolved or suspended in a hydrocarbon, and a preheated reaction assistant hydrocarbon which acts as a heat transfer agent and a hydrogen source, and then pyrolyzing said steroidal compound.

BRIEF DESCRIPTION OF THE DRAWING

A more complete appreciation of the invention and many of the attendant advantages thereof will be readily attained as the same becomes better understood by reference to the following detailed description when considered in connection with the accompanying drawing, wherein:

One preferred method of conducting the process of this invention is illustrated in FIG. 1.

DETAILED DESCRIPTION OF THE PREFERRED EMBODIMENTS

The present invention provides a process for producing steroidal 19-nor-3-hydroxy-1,3,5(10)-trienes in which ring A has the formula,

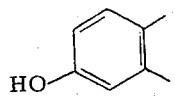

wherein a solution of a steroidal 10-methyl-1,4-dien-3-one, in which ring A has the formula,

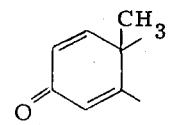

dissolved or suspended in a hydrocarbon, which readily dissolves said steroidal 10-methyl-1,4-dien-3-one, is mixed with a preheated reaction assistant hydrocarbon, which acts as a heat transfer agent and a hydrogen source, and then is subjected to pyrolysis.

Suitable steroidal 10-methyl-1, 4-dien-3-one starting materials for use in the process of this invention include those which are stable under the reaction conditions. Such suitable starting materials include androst-1, 4-dien-3, 17-dione, 17-hydroxyandrost-1,4,6-trien-3-one, androst-1,4,6-trien-3, 17-dione, 17-hydroxyandrost-1,4,6-trien-3-one, pregn-1,4-dien-3, 20-dione and the like. While androst-1,4-dien-3, 17-dione and estrone are stable at temperatures below 300° C for long periods of time, the amount of undesired products formed by decomposition increases with increase in residence times in the reaction zone at temperatures over 300° C.

Consequently, in addition to rapid cooling of the pyrolysis product estrone to a temperature below 300° C, rapid heating of the starting androst-1,4-dien-3,17-dione to the reaction temperature plays an important role in avoiding unfavorable side reactions. Furthermore, proper reactor design and proper choice of reaction conditions such as reaction temperature, reaction time (residence time in the reaction zone) and flow rate of the reaction liquid or gas are important to obtain estrone in high yield and selectivity.

The steroidal 10-methyl-1, 4-dien-3-one starting material is fed to the reactor as a solution or suspension. Suitable hydrocarbons used to dissolve or suspend the steroidal 10-methyl-1, 4-dien-3-one starting material include aromatic hydrocarbons such as benzene, toluene, xylene, ethylbenzene and the like; and hydrocarbons such as tetralin, decalin, light oil, kerosene, mineral oil and the like. A mixture of an aromatic hydrocarbon and a hydrocarbon such as tetralin, decalin, light oil, kerosene or naphtha can also be employed.

Normally, the hydrocarbon is used in an amount sufficient to dissolve the starting steroid.

The amount of the hydrocarbon to be used should be 1 – 100 times that of the steroidal compound, preferably 2 – 50 times.

It is preferred to employ an aromatic hydrocarbon which can readily dissolve said steroidal compound, since the use of a small amount of an aromatic hydrocarbon favors rapid heating of the starting steroidal compound to the reaction temperature.

It is also preferred to heat the solution or suspension of the steroidal compound in the preheater to a temperature of 300° C below which the steroidal compound is stable, since this preheating also favors rapid heating of the starting steroidal compound.

The pyrolysis step requires two hydrogen atoms which are supplied from the reaction assistant hydrocarbon. Besides being a hydrogen source, the hydrocarbon is also a heat transfer agent as well as a reaction solvent. The suitable hydrocarbons for use in the process of this invention are those which can be cracked to a significant degree at the reaction temperature to liberate hydrogen. Such suitable hydrocarbons include ethane, propane, butane, pentane, heptane, octane, kerosene, light oil, tetralin, naphtha, decalin, mineral oil, cyclohexane, methylcyclohexane, higher aliphatic hydrocarbons and the like.

Among these hydrocarbons, ethane, propane, butane, pentane, heptane, kerosene, light oil, tetralin, naphtha, decalin, mineral oil and cyclohexane are preferred. The amount of the hydrocarbon to be used is 10 – 2,000 times the amount of the starting steroid, preferably 20 – 1,000 times.

The hydrocarbon is heated by the preheater to a sufficiently high temperature to supply most of the heat required for conducting the pyrolysis. Normally, the hydrocarbon is heated to a temperature as high as the reaction temperature + 200° C, i.e., 400° – 850° C, preferably 450° – 750° C, and then is mixed with the hydrocarbon solution of the starting steroid preferably heated to a temperature up to 300° C.

It is to be noted that near the opening to the mixer, the feed pipe for the hydrocarbon solution of the starting steroid is heated by the preheated reaction assistant hydrocarbon. High temperature of the surface of this feed pipe near the opening to the mixer distinctly tends to cause tar and coke formation, which can lead to blockages of the feed pipe and makes continuous operation difficult. To prevent such tar and coke formation, it is preferred to maintain the surface of the feed pipe near the opening at a temperature below 450° C, preferably 400° C. Although this lower temperature for the hydrocarbon solution of the starting steroid does not favor rapid heating of the starting steroid, this disadvantage is outweighed by improved process control. In addition to temperature control of the feed pipe of the starting steroidal compound, the presence of water or hydrogen in the reaction mixture aids in preventing tar and coke formation. In this manner, the starting steroid can be heated rapidly to the reaction temperature by admixing the hydrocarbon solution of the starting steroid and the preheated reaction assistant hydrocarbon in the mixer. Then, the pyrolysis of the starting steroid is carried out by feeding the mixed hydrocarbon solution of the starting steroid to the reactor.

The pyrolysis of the steroidal 10-methyl-1, 4-dien-3-one starting material is carried out at a temperature of 450 – 700° C, preferably 500° – 650° C. Reaction times vary widely depending upon the reaction temperature, and range from 0.001 second to 60 seconds, more preferably from 0.01 second to 30 seconds. It is necessary that the reaction gas have sufficient flow rate to maintain plug flow characteristics, and from an engineering standpoint, it is preferred to carry out the reacton in a turbulent flow region. In view of the above, it is preferred that the linear gas velocity in the tubular reactor be 10 – 70,000 cm/sec., preferably 30 – 30,000 cm/sec., highly dependent upon the size of the tubular reactor.

An outstanding feature of the process of the present invention is that most of the heat required for the pyrolysis and heating of the reaction mixture can be supplied by the preheater, so that the reactor plays a role similar to an adiabatic reactor which is not externally heated during operation. As a result local overheating in the reactor is avoided, maintenance of constant elevated temperatures is permitted, stable operation in technical production is facilitated and production of the steroidal 19-nor-3-hydroxy-1,3,5(10)-triene in high yield is possible. Upon completion of the reaction, the reaction mixture is rapidly cooled to a temperature below 300° C, at which the steroidal 19-nor-3-hydroxy-1,3,5(10)-trienes are stable. When a hydrocarbon having a low boiling point, such as ethane, propane, butane, naphtha, light oil or the like, is used as the reaction assistant hydrocarbon, it is preferred to quench the reaction mixture by means of a direct contact with a high boiling hydrocarbon such as kerosene, mineral oil and the like. The crystalline steroidal 19-nor-3-hydroxy-1,3,5(10)-trienes formed by cooling the reaction mixture to room temperature are separated by filtration.

As previously described, the advantages of the process of the present invention are:

1. the preheated reaction assistant hydrocarbon facilitates the heat transfer of the starting steroidal compound and permits the rapid heating of the starting steroidal compound to the reaction temperature;

2. the rapid heating of the starting steroidal compound suppresses side reactions and greatly increases the yield;

3. proper choice of reaction conditions increases the yield;

4. use of the preheated reaction assistant hydrocarbon to supply the principal amount of heat permits maintenance of constant elevated temperatures in the reactor and facilitates stable continuous operation; and 5. proper choice of the temperature of the feed pipe for the starting steroidal compound near the opening to the mixer prevents tar and coke formation, and makes possible the continuous production of the steroidal 19-nor-3-hydroxy-1,3,5(10)-trienes on an industrial scale.

The process of the present invention, therefore, has advantages over the well-known processes and is especially suitable for a continuous process for the production of the steroidal 19-nor-3-hydroxy-1,3,5(10)-trienes on an industrial scale.

Having generally described this invention, a more complete understanding can be obtained by reference examples and examples which are provided herein for purposes of illustration only and are not intended to be limiting in any manner.

The reaction apparatus shown in FIG. 1 is used to carry out the process of this invention in the following examples.

The reaction assistant hydrocarbon which acts as a heat transfer agent and a hydrogen source is fed from the storage tank 1 to the preheater 3 and led to the mixer 5. A solution of a steroidal 10-methyl-1, 4-dien-3-one dissolved or suspended in a hydrocarbon is fed from the storage tank 2 to the preheater 4 and led to the mixer 5 where it is mixed with the preheated hydrocarbon, and then passed through the tubular reactor 6 where it is subjected to pyrolysis. The reaction mixture, after leaving the reactor 6, is cooled by the heat exchanger 7 and then collected in the receiver 8.

EXAMPLE 1

Employing the reaction apparatus shown in FIG. 1, the reaction assistant kerosene was fed at a rate of 145 ml/min. and passed through the preheater for the reaction assistant (SUS 32, 5 mm$\phi$ × 4 m), where it was heated to a temperature of 590° C, led to the reactor (SUS 32, 5mm$\phi$ × 2m) and then to the heat exchanger where it was rapidly cooled to a temperature below 200° C, and finally collected in the reaction liquid receiver. A solution of androst-1, 4-dien-3, 17-dione dissolved in 20 fold xylene was fed at a rate of 6 ml/min. and passed through the mixer where it was mixed with the preheated reaction assistant kerosene, and then led to the reactor where it was subjected to continuous pyrolysis at a temperature of 550° C under a pressure of 10 kg/cm² for a period of 0.6 second. The reaction products, after leaving the reactor, were cooled in the heat exchanger and finally collected in the reaction liquid receiver. Samples were taken at intervals from the reaction mixture and analyzed. Analysis by gas chromatography of the reaction liquid under steady state conditions showed a 89.4% conversion of the starting steroid, and a 81.4% selectivity of estrone.

EXAMPLE 2

This example illustrates the effect of preheating the starting steroidal compound to a temperature up to 300° C. Employing the same reaction apparatus as that of Example 1, the reaction assistant kerosene was fed at a rate of 145 ml/min. and passed through the preheater where it was heated to a temperature of 570° – 580° C, and led to the reactor. A solution of androst-1, 4-dien-3, 17-dione dissolved in 20 fold xylene was fed at a rate of 6 ml/min. and passed through the preheater where it was heated to a temperature of 200° C, and led to the mixer where it was mixed with the reaction assistant, and then to the reactor where it was subjected to pyrolysis at a temperature of 550° C under a pressure of 10 kg/cm² for a period of 0.6 second. Analysis by gas chromatography of the reaction liquid under steady state conditions showed a 92.0% conversion, and a 84.1% selectivity of estrone.

EXAMPLES 3 – 19

Example 2 was repeated, except that the reaction conditions were varied as indicated in Table 1. The results are shown in Table 1.

EXAMPLES 20 – 26

Example 2 was repeated, except that the reaction assistant hydrocarbon and/or the solvent used to dissolve androst-1, 4-dien-3, 17-dione, and the reaction conditions were varied as indicated in Table 2. The results are shown in Table 2.

EXAMPLE 27

This example illustrates the importance of temperature control of the

TABLE 1

| Example No. | Feed Rate of Reaction Assistant ml/min | Starting Steroid Solution Concentration wt % | Starting Steroid Solution Feed Rate ml/min | Reaction Temperature °C | Reaction Pressure kg/cm² | Reaction Time sec. | Conversion % | Selectivity % |
|---|---|---|---|---|---|---|---|---|
| 3* | 50 | 5.0 | 6 | 420 | 20 | 5.0 | 85.4 | 35.1 |
| 4 | 145 | 5.0 | 6 | 480 | 20 | 1.5 | 34.9 | 67.2 |
| 5 | 145 | 5.0 | 6 | 510 | 30 | 2.0 | 75.3 | 77.0 |
| 6 | 175 | 5.0 | 6 | 520 | 20 | 1.0 | 75.6 | 78.0 |
| 7 | 100 | 5.0 | 6 | 520 | 20 | 1.8 | 86.8 | 76.0 |
| 8 | 145 | 5.0 | 6 | 520 | 20 | 1.3 | 84.0 | 78.0 |
| 9 | 145 | 10.0 | 6 | 520 | 20 | 1.3 | 85.2 | 77.5 |
| 10 | 145 | 5.0 | 6 | 535 | 20 | 1.0 | 75.8 | 84.2 |
| 11 | 145 | 5.0 | 6 | 550 | 5 | 0.3 | 70.5 | 87.1 |
| 12 | 145 | 5.0 | 6 | 560 | 10 | 0.6 | 95.4 | 83.0 |
| 13 | 145 | 5.0 | 6 | 600 | 10 | 0.5 | 94.8 | 70.8 |
| 14 | 145 | 5.0 | 6 | 500 | 1 | 5.0 | 82.1 | 85.4 |
| 15 | 145 | 5.0 | 6 | 530 | 1 | 1.0 | 81.3 | 85.1 |
| 16 | 145 | 5.0 | 6 | 550 | 1 | 0.3 | 76.6 | 83.0 |
| 17 | 145 | 15.0 | 6 | 550 | 1 | 0.3 | 79.1 | 83.7 |
| 18 | 145 | 20.0 | 6 | 550 | 1 | 0.3 | 77.4 | 85.2 |
| 19 | 145 | 5.0 | 6 | 600 | 1 | 0.07 | 82.1 | 84.5 |

*The results of Example 3 were obtained under conditions of improper temperature and reaction time control and it is problematic whether the results of this example are reproducible.

TABLE 2

| Example No. | Reaction Assistant Hydrocarbon | Feed Rate of Reaction Assistant ml/min. | Solvent | Concentration wt. % | Feed Rate ml/min. | Reaction Temperature °C | Reaction Pressure kg/cm² | Reaction Time sec. | Conversion % | Selectivity % |
|---|---|---|---|---|---|---|---|---|---|---|
| 20 | Tetralin | 145 | Xylene | 5.0 | 6 | 550 | 5 | 0.3 | 78.8 | 81.2 |
| 21 | Decalin | 145 | Xylene | 5.0 | 6 | 550 | 5 | 0.3 | 80.4 | 78.7 |

TABLE 2-continued

| | Reaction Conditions | | | | | | | | |
| --- | --- | --- | --- | --- | --- | --- | --- | --- | --- |
| | Reaction Assistant | Feed Rate of Reaction Assistant ml/min. | Starting Steroid Solution | | | Reaction Temperature °C | Reaction Pressure kg/cm² | Reaction Time sec. | Reaction Result | |
| Example No. | Hydro-Carbon | | Solvent | Concentration wt. % | Feed Rate ml/min. | | | | Conversion % | Selectivity % |
| 22 | Propane | 145 | Xylene | 5.0 | 6 | 550 | 5 | 0.3 | 73.6 | 85.9 |
| 23 | Naphtha | 145 | Xylene | 5.0 | 6 | 550 | 5 | 0.3 | 71.2 | 88.1 |
| 24 | Kerosene | 145 | Decalin | 3.0 | 6 | 550 | 5 | 0.3 | 72.4 | 85.7 |
| 25 | Kerosene | 145 | Tetralin | 5.0 | 6 | 550 | 5 | 0.3 | 71.0 | 86.2 |
| 26 | Kerosene | 145 | Kerosene | 1.0 | 6 | 550 | 5 | 0.3 | 72.1 | 88.3 | feed pipe of the starting steroidal compound. Employing naphtha and toluene, respectively, as the reaction assistant hydrocarbon and the solvent for androst-1,4-dien-3, 17-dione, Example 2 was repeated except that the feed pipe of androst-1, 4-dien-3, 17-dione near the opening to the mixer, 5 cm long from the end of the feed pipe, was substituted by a jacketed pipe in which the inner tube had an inside diameter of 1 mm and an outside diameter of 3mm, and the outside tube had an inside diameter of 6 mm and an outside diameter of 10 mm. The temperature of the surface of the feed pipe near the opening to the mixer was controlled by passing nitrogen through the outside tube. When nitrogen was not passed through the outside tube, the feed pipe was blocked after 7 hours from the start of feeding the steroidal solution because of tar and coke formation. When the surface of the feed pipe near the opening to the mixer was maintained at a temperature of 500° C, the feed pipe was blocked after 24 hours. When the surface of the feed pipe near the opening to the mixer was maintained at a temperature of 400° C, the steroidal solution could be passed through the feed pipe without formation of tar and coke for a long period of time.

EXAMPLE 28

Employing androst-1,4,6-trien-3, 17-dione in place of androst-1, 4-dien-3, 17-dione, Example 1 was repeated. Analysis by gas chromatography of the reaction liquid under steady state conditions showed a 92.3% conversion of the starting steroid, and a 83.7% selectivity of 3-hydroxyestra-1, 3,5(10), 6-tetraen-17one.

REFERENCE EXAMPLE 1

This reference example illustrates the disadvantage of heating the solution of the starting steroidal compound dissolved in a large amount of the reaction assistant hydrocarbon to the reaction temperature. A solution of androst-1, 4-dien-3, 17-dione dissolved in 500 fold kerosene was fed at a rate of 145 ml/min. and passed through the preheater (SUS 32, 5 mm$\phi$ × 2 m) where it was heated to a temperature of 590° C, and then to the reactor (SUS 32, 5 mm$\phi$ × 2 m) where it was subjected to pyrolysis at a temperature of 550° C under a pressure of 1 kg/cm² for a period of 0.3 second. Analysis by gas chromatography of the reaction liquid under steady state conditions showed a 99.7% conversion, and a 47.2% selectivity of estrone. It can be seen that, as compared with the result of the corresponding Example 16, the selectivity of this reference example is considerably low.

REFERENCE EXAMPLES 2 – 3

Reference Example 1 was repeated except that the reaction temperature and reaction time were varied as indicated in Table 3. The results are shown in Table 3. It can also be seen that, as compared with the results of the corresponding Examples 14 and 19, the selectivities of these reference examples are considerably low. The results are shown in Table 3.

TABLE 3

| Reference Example No. | Temperature of Reaction Liquid after Preheating °C | Reaction Temperature °C | Reaction Time sec. | Conversion % | Selectivity % |
| --- | --- | --- | --- | --- | --- |
| 2 | 550 | 500 | 5.0 | 97.4 | 55.1 |
| 3 | 630 | 600 | 0.07 | 100 | 37.6 |

REFERENCE EXAMPLE 4

A solution of androst-1, 4-dien-3, 17-dione, dissolved in 500 fold kerosene was fed at a rate of 145 ml/min. and passed through the preheater (SUS 32, 5 mm$\phi$ × 4 m) heated to a temperature of 600° C and then the reactor (SUS 32, 5 mm$\phi$ × 2 m) where it was subjected to pyrolysis at a temperature of 550° C under a pressure of 10 kg/cm² for a period of 0.6 second. Analysis by gas chromatography of the reaction liquid under steady state conditions showed a 78.9% conversion and a 72.4% selectivity.

REFERENCE EXAMPLES 5 – 7

Reference Example 4 was repeated except that the reaction temperature, reaction pressure and reaction time were varied as indicated in Table 4. The results are shown in Table 4.

The results of Reference examples 4 – 7 were also obtained under conditions of improper temperature and reaction time control and it is problematic whether the results of these particular examples are reproducible.

TABLE 4

| Reference Example No. | Reaction Temperature °C | Reaction Pressure kg/cm² | Reaction Time sec. | Conversion % | Selectivity % |
| --- | --- | --- | --- | --- | --- |
| 5 | 520 | 20 | 1.0 | 31.5 | 54.0 |
| 6 | 540 | 20 | 1.0 | 51.5 | 78.7 |
| 7 | 560 | 20 | 1.2 | 87.3 | 72.1 |

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A process for producing a steroidal 19-nor-3-hydroxy-1, 3, 5 (10)-triene, which comprises:
   mixing a steroidal 10-methyl-1, 4-diene-3-one in a hydrocarbon such that said steroid is dissolved or suspended in said hydrocarbon;
   preheating a hydrocarbon heat transfer agent to a temperature suitable for pyrolysis of said steroid;
   mixing said preheated hydrocarbon and said steroid-hydrocarbon mixture;
   and pyrolyzing said steroidal compound.

2. The process of claim 1, wherein the steroidal 10-methyl-1,4-dien-3-one is androst-1,4-dien-3, 17-dione, and the steroidal 19-nor-3-hydroxy-1,3,5(10)-triene is 3-hydroxyestra-1,3,5(10)-trien-17-one.

3. The process of claim 1, wherein the steroidal 10-methyl-1,4-dien-3-one is androst-1,4,6-trien-3, 17-dione, and the steroidal 19-nor-3-hydroxy-1, 3,5(10)-triene is 3-hydroxyestra-1,3,5(10), 6-tetraen-17-one.

4. The process of claim 1, wherein the preheated hydrocarbon is capable of being cracked to a significant degree at the reaction temperature to liberate hydrogen.

5. The process of claim 4, wherein the preheated hydrocarbon is selected from the group consisting of ethane, propane, butane, pentane, heptane, kerosene, light oil, tetralin, naphtha, decalin, mineral oil and cyclohexane.

6. The process of claim 1, wherein the amount of the preheated hydrocarbon to be used is 20 – 1,000 times as large as that of the steroidal 10-methyl-1,4-dien-3-one.

7. The process of claim 1, wherein the hydrocarbon used to dissolve or suspend the steroidal 10-methyl-1,4-dien-3-one dissolves said steroidal compound readily.

8. The process of claim 7, wherein the hydrocarbon is selected from the group consisting of an aromatic hydrocarbon, and a mixture of an aromatic hydrocarbon and a hydrocarbon selected from the group consisting of tetralin, decalin, light oil, kerosene and naphtha.

9. The process of claim 8, wherein the aromatic hydrocarbon is selected from the group consisting of benzene, toluene, xylene and ethylbenzene.

10. The process of claim 1, wherein the amount of the hydrocarbon to be used for dissolving or suspending the steroidal 10-methyl-1, 4-dien-3-one is 2 – 50 times as large as that of the steroidal 10-methyl-1, 4-dien-3-one.

11. The process of claim 1, wherein the temperature of the preheated hydrocarbon is 450° – 750° C.

12. The process of claim 1, wherein the solution of the steroidal 10-methyl-1, 4-dien-3-one is preheated to a temperature up to 300° C.

13. The process of claim 1, wherein the surface temperature of the inlet feed pipe of the hydrocarbon solution of the steroidal 10-methyl-1, 4-dien-3-one near the opening of the mixer is below 400° C.

14. The process of claim 1, wherein the pyrolysis is carried out under substantially adiabatic conditions at a temperature of 500° – 650° C and a linear gas velocity of 30 – 30,000 cm/second for a period of 0.01 – 30 seconds.

15. The process of claim 1, wherein 19-nor-3-hydroxy-1,3,5(10)-trienes are produced by admixing a hydrocarbon which is capable of being cracked to a significant degree at the reaction temperature to liberate hydrogen and preheated to a temperature of 450° – 750° C so as to supply most of the heat required for conducting the pyrolysis, and a steroidal 10-methyl-1, 4-dien-3-one dissolved or suspended in an aromatic hydrocarbon selected from the group consisting of benzene, toluene, xylene, ethylbenzene or a mixture of said aromatic hydrocarbons and a hydrocarbon selected from the group consisting of tetralin, decalin, light oil, kerosene and naphtha, in order to rapidly heat said steroidal 10-methyl-1, 4-dien-3-one, and thereafter pyrolyzing the steroidal 10-methyl-1, 4-dien-3-one under substantially adiabatic conditions at a temperature of 500° – 650° C, and a linear gas velocity of 30 – 30,000 cm/second for a period of 0.01 – 30 seconds.

* * * * *